United States Patent [19]

Jeraci et al.

[11] Patent Number: 5,801,300
[45] Date of Patent: Sep. 1, 1998

[54] METHOD FOR DETERMINING GLYCOL AND FORMALDEHYDE CONTAMINANTS IN GROUND WATER SAMPLES

[75] Inventors: Joseph L. Jeraci, Liverpool; David Prichard, Brewerton, both of N.Y.

[73] Assignee: Life Science Laboratories, Inc., East Syracuse, N.Y.

[21] Appl. No.: 834,484

[22] Filed: Apr. 14, 1997

Related U.S. Application Data

[60] Provisional application No. 60/015,845 Apr. 19, 1996.
[51] Int. Cl.$^6$ .................. C02B 1/14; G01N 21/00; B65B 1/30
[52] U.S. Cl. .................. 73/53.01; 73/61.43; 422/68.1; 423/264
[58] Field of Search .................. 73/53.1, 61.43; 422/68.1; 423/264

[56] References Cited

U.S. PATENT DOCUMENTS

| | | | |
|---|---|---|---|
| 2,009,943 | 7/1935 | Munsell et al. | 88/14 |
| 4,157,300 | 6/1979 | Junkermann et al. | 210/40 |
| 4,466,942 | 8/1984 | Rogers | 422/61 |
| 5,278,193 | 1/1994 | Eiffler et al. | 521/31 |
| 5,295,761 | 3/1994 | Heacock et al. | 405/128 |
| 5,576,482 | 11/1996 | Russ et al. | 73/61.43 |
| 5,585,550 | 12/1996 | Frank | 73/61.43 |

*Primary Examiner*—Hezron E. Williams
*Assistant Examiner*—J. David Wiggins
*Attorney, Agent, or Firm*—Bauer & Schaffer

[57] ABSTRACT

A method for the qualitative determination of the visible levels of glycol and/or formaldehyde at significant concentrations greater than 10 ppm (10 ppm–10,000 ppm range) in a water sample, in which the sample is treated first with periodic acid, then with iodide-thiosulfate and finally with acetyl acetone to yield a yellow color without the benefit of heat. This yellow color is visible to the naked eye and proportional to the amount of contaminants ethylene glycol, propylene glycol and/or formaldehyde present in the original water sample.

5 Claims, No Drawings

METHOD FOR DETERMINING GLYCOL AND FORMALDEHYDE CONTAMINANTS IN GROUND WATER SAMPLES

RELATED APPLICATION

This application claims the benefit of U.S. Provisional Application Ser. No. 60/015,845 filed on Apr.19, 1996.

BACKGROUND OF THE INVENTION

The present invention relates to a method of testing for the presence of glycol in aqueous samples. More particularly, this invention relates to a test procedure that is suitable for field testing for the existence of glycol contamination of water and to the apparatus for carrying out the test procedure.

Glycols, such as propylene and ethylene have been found to be contaminants in the ground and water as a result of many industrial activities. These activities could be related to any number of industries, in which soil and water are a part of the industrial process and/or resultant waste product. The invention is particularly suitable in the field of chemical processing and product formation; treatment of aviation facilities' water, construction and/or mining. These contaminants when dumped to the ground or in water have been found to have adverse effect on the health of those who become exposed to them. As a result governments at the local, state and federal levels have instituted regulations to strictly limit the concentrations of these contaminants in the environment. In an effort to abide and conform to these regulations, many of the industries generating these contaminants are actively seeking ways and means by which they can monitor the concentration of these contaminants, and if need be, to arrange for environmental remediation for the return of ground water to safer limits.

A laboratory method for determining, extremely low levels of contaminants in water is set out in the standard method issued by the New York State Department of Environmental Conservation, NYSDEC 89-9. This method is complicated and involved and requires a sample of a contaminated aqueous solution to be subjected to several reactive agents so that finally an acetyl acetone reaction with the formaldehyde content of the sample is produced. This reaction requires high heat for an extended period of time. This method is limited to obtaining accurate quantifiable results in the lowest areas of contaminant proportion, i.e. 0.1–10 parts per million. It also requires observation of the results with a spectrophotometer. It is also limited to use in a laboratory where a source of heat and the necessary equipment are readily available.

On the other hand, it is frequently necessary to make field analyses of contaminated water and other fluids, particularly during construction, mining, and de-icing of airplanes. At these times and places there is no time to set up laboratory facilities so as to provide the necessary heat and other means for obtaining and quantifying the results.

Furthermore, the need for quantifiable results at very low concentrations is only of limited importance and application. Generally, what is required is a qualitative analysis of the levels of contaminants in the water so as to provide readily usable in situ information. Consequently, the highly sophisticated method of NYSDEC 89.9 is unwieldy and costly for the on site needs of industry. The NYSDEC 89.9 method is time consuming and would unduly interfere with the industrial program underway.

It is, therefore, the object of the present invention to provide a simple, rapid, reliable and highly portable test for the screening of such contaminants as ethylene glycol, propylene glycol and formaldehyde at significant concentration levels found on site.

Another object of the present invention is to provide for a test that can be completed in the field outside and away from the laboratory within minutes.

Another object of the present invention is to provide for a qualitative analysis of such contaminants as propylene glycol, ethylene glycol and formaldehyde without a great number of otherwise bulky, expensive and fragile testing glassware.

Another object of the invention is to provide for a qualitative analysis of such water contaminants as propylene glycol, ethylene glycol and formaldehyde without an ultraviolet/visible spectrophotometer, vortex mixer, water bath; and other expensive equipment.

A further object of the present invention is to eliminate the immediate need for a qualified chemist or at the very least a laboratory technician trained to perform an on-site analysis.

These and further objects of the present invention will become apparent from the following description of the preferred embodiments thereof.

BRIEF SUMMARY OF THE INVENTION

A method for the qualitative determination of the visible levels of glycols and/or formaldehyde at significant concentrations in a water sample, in which the sample is treated first with periodic acid, then with iodide-thiosulfate and finally with acetyl acetone to yield a yellow color without the benefit of heat. This yellow color is visible to the naked eye and proportional to the amount of contaminants present in the original water sample.

DESCRIPTION OF THE INVENTION

Briefly, the present invention is directed to a process for testing a predetermined sample of water suspected of having glycol and/or formaldehyde content. To four drops of this sample two drops of a periodic acid solution is added thereby oxidizing any Glycols in the sample of formaldehyde. Thereafter, two drops of iodide-thiosulfate solution is added to the sample to further reduce the remaining periodic and iodic acids. To this reduced sample eight drops of acetyl acetone are introduced. The formaldehyde present after the oxidation of the glycol and/or existing in the original sample reacts, without the addition of any catalytic feature such as heat or any other reactant, with the acetyl acetone to form diacetyldihydrolutidine (DDL) resulting in the formation of a fluid having a yellow color. The colored fluid is thereupon compared with a selected number of similarly colored standards qualitatively indicative of selected levels of contamination.

In the present invention it is to be noted that not only is the initial sample cold (it may even be colder than room temperature) the entire process is conducted without any heat being applied to the sample. This feature has great advantage, in testing de-icing liquid at the airport in the middle of winter.

The entire sample is minuscule in size comprising no more than four drops, to which is added another twelve drops of reactant agents. Thus, large equipment usually associated with laboratory testing is unnecessary. A drop as used therein is of the size which is normally extruded through small plastic squeeze bottles of the type, used to dispense fluid medication or ophthalmological fluids.

In the present invention it is preferred to employ: a periodic acid solution, having a concentration of 0.02 Molar, (4.6 grams periodic acid/liter of deionized water); a potassium iodide/sodium thiosulfate solution containing 25.9 grams potassium iodide and 17.5 grams sodium thiosulfate per liter of deionized water; and acetyl acetone solution containing 150 grams ammonium acetate, 3 milliliters acetic acid and 2 milliliters of 2,4 pentanedione per liter of deionized water.

The standards to which the yellow color is compared are comprised of glycol solutions of 10 to 10,000 milligrams glycol per liter of deionized water. The specific glycol is selected to conform to the glycol compound which the operator believes he or she is testing for and therefore may be selected as necessary.

In furnishing the present invention for in situ use, it is the object of the present invention to provide all of the materials in a small kit like form. Thus, each of the reagents can be bottled in the small plastic dispenser bottles of the type used in ophthalmological or pharmacological dispensing. A small test tube like container (with cover) is provided in which the test sample drops and the reagent drops are placed and allowed to react. The standards are premixed and bottled in separate, sealed, small, cylindrical containers. Preferably a set of four such standard bottles at selected levels of glycol within the range to be tested will be provided between the range of ten (10) ppm to ten thousand (10,000) ppm of glycol. The user, of course, being interested in a qualitative analysis will compare the resultant test sample color to the closest of the supplied standard colors. The entire kit can be put together in no larger than a rectilinear box having its larger dimension between 8 and 12 inches.

EXAMPLE 1) admixing to a sample of water which is to be tested, an amount of approximately equal to one half (½) of said sample with an aqueous solution of periodic acid and allowing said admixture to stand for a sufficient time to permit oxidation of the glycol to formaldehyde;

2) thereafter, adding to the resultant of step 1, an amount equal to said periodic acid of an aqueous solution of iodide-thiosulfate and mixing, said mixture until the iodide-thiosulfate is completely dispersed and any remaining periodic acid in said resultant is thoroughly reduced;

3) thereafter, adding to the resultant of step 2, an equal amount to the total amount of the mixture, an aqueous solution of acetyl acetone and mixing until acetyl acetone is completely dispersed and the formaldehyde is reacted to form diacetyl:dihydrolutidine (DDL) having a yellow color; and 4) finally, comparing the resultant of step 3 to a pre-selected colored standard.

As has been seen, this analytical method is advantageously used in the field as a quick way to screen samples for the presence of glycols. It is cheap, efficient, easily used and satisfied each of the objects enumerated earlier.

Various modifications and changes have been disclosed herein, and others will be apparent to those skilled in this art. Therefore, it is to be understood that the present disclosure is by way of illustrating and not limiting of the present invention.

What is claimed is:

1. A method for testing water samples for the presence of glycol and formaldehyde contamination comprising the steps of 1) admixing to a sample of water which is to be tested, an amount of approximately equal to one half (½) of said sample with a first aqueous solution of periodic acid to form an admixture and allowing said admixture to stand for a sufficient time to permit oxidation of the glycol to formaldehyde in a first resultant solution;

2) thereafter, adding to the first resultant solution of step 1, an amount equal to said periodic acid to form a mixture of a second aqueous solution of iodide-thiosulfate and mixing, said mixture until the iodide-thiosulfate is completely dispersed and any remaining periodic acid in said resultant is thoroughly reduced to form a second resultant solution;

3) thereafter, adding to the second resultant solution of step 2, an equal amount to the total amount of the mixture, a third aqueous solution of acetyl acetone and mixing until acetyl acetone is completely dispersed and the formaldehyde is reacted to form diacetyldihydrolutidine (DDL) in a third resultant solution having a yellow color; and 4) finally, comparing the third resultant solution of step 3 to a pre-selected colored standard.

2. The method according to claim 1 for in situ field testing, wherein said sample is provided in the amount of four drops, the periodic acid in the amount of two drops, the iodide-thiosulfate in the amount of two drops and the acetyl acetone in the amount of eight drops, said admixture taking place in an open container at ambient temperature and pressure in the absence of any catalyst.

3. The method according to claim 1, wherein in step 1, the admixture is allowed to stand for five to ten minutes.

4. The method according to claim 1, wherein the concentration of the aqueous first solution of periodic acid is 0.02M.

5. The method according to claim 1, the aqueous second solution of iodide thiosulfate contains 2.59 gr potassium Iodide and 1.75 g of Sodium thiosulfate in 100 mls of water.

* * * * *